(12) United States Patent
Achilefu et al.

(10) Patent No.: US 6,264,919 B1
(45) Date of Patent: Jul. 24, 2001

(54) INDOCYANINE DYES

(75) Inventors: Samuel Achilefu, St. Louis; Raghavan Rajagopalan, Maryland Heights; Richard B. Dorshow, St. Louis; Joseph E. Bugaj, St. Charles, all of MO (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/636,170

(22) Filed: Aug. 10, 2000

Related U.S. Application Data

(62) Division of application No. 09/484,323, filed on Jan. 18, 2000.

(51) Int. Cl.[7] .............................. A61B 10/00; A61B 5/00; A61B 8/00
(52) U.S. Cl. ..................... 424/9.6; 424/9.61; 424/1.11; 424/1.65; 424/9.1; 252/301.16
(58) Field of Search .................................. 424/1.11, 9.1, 424/9.6, 9.61, 1.65; 252/301.16, 301.17, 301.19, 301.21, 301.34, 301.35

(56) References Cited

PUBLICATIONS

Bergmark et al, 1990, J. Phys. Chem., vol. 94, pp. 5020–5022.*

* cited by examiner

*Primary Examiner*—Dameron L. Jones
(74) *Attorney, Agent, or Firm*—Lawrence L. Limpus

(57) ABSTRACT

The sensitivity and specificity of the optical modality can be enhanced by the use of highly absorbing dyes as contrast agents. Novel indocyanine dyes that absorb and emit light in the near infrared region of electromagnetic spectrum are disclosed. These dyes are useful for imaging, diagnosis and therapy of various diseased states. Particularly, the molecules of the invention are useful for optical diagnostic imaging and therapy, in endoscopic applications for the detection of tumors and other abnormalities, for localized therapy, for photoacoustic tumor imaging, detection and therapy, and for sonofluorescence tumor imaging, detection and therapy.

4 Claims, 3 Drawing Sheets

Preparation of bis-carboxylates; A=$CH_2$ or $CH_2OCH_2$;
R=COOH; R'=COOH,NHFmoc;$CO_2$t-Bu;$SO_3$
$R_1$=$R_2$=H(Formula 1) or $R_1$,$R_2$=fused phenyl (Formula 2)

Preparation of polyhydroxy-carboxylic acid cyanine dyes

Preparation of Tetra-carboxylates; A=CH₂ or CH₂OCH₂;
R₁=R₂=H (Formula 1) or R₁,R₂=fused phenyl (Formula 2)

Synthesis of non-aggregating cyanine dyes

Synthesis of "tunable" cyanine dyes

Representative scheme for the preparation of bioconjugates; $A=CH_2$ or $CH_2OCH_2$, $R_1=R_2=H$ (Formula 1) or $R_1,R_2=$ fused phenyl Formula 2):
AA= Amino Acids; R=CONH peptide; R'=R (Bis conjugate) or COOH (Mono conjugate)
(P)=Solid support; (P')=Presence or absence depends on R' definition

```
                              SEQUENCE LISTING

<160> NUMBER OF SEQ ID NOS:  8

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:Octreotide
<221> NAME/KEY: SITE
<222> LOCATION: (1)
<223> OTHER INFORMATION: This is D-phenylalanine
<221> NAME/KEY: DISULFID
<222> LOCATION: (2)..(7)
<221> NAME/KEY: SITE
<222> LOCATION: (4)
<223> OTHER INFORMATION: This is D-tryptophan
<221> NAME/KEY: SITE
<222> LOCATION: (8)
<223> OTHER INFORMATION: This C-terminal residue ends with a hydroxyl

<400> SEQUENCE: 1

Phe Cys Tyr Trp Lys Thr Cys Thr
  1               5

<210> SEQ ID NO 2
<211> LENGTH: 11
<212> TYPE: PRT
<213> ORGANISM: Artificial Sequence
<220> FEATURE:
<221> NAME/KEY: SITE
<222> LOCATION: (11)
<223> OTHER INFORMATION: This C-terminal amino acid ends with an NH2
<223> OTHER INFORMATION: Description of Artificial Sequence:ANALOG OF
      BOMBESIN.

<400> SEQUENCE: 2

Gly Ser Gly Gln Trp Ala Val Gly His Leu Met
  1               5                  10

<210> SEQ ID NO 3
<211> LENGTH: 11
<212> TYPE: PRT
<213> ORGANISM: Artificial Sequence
<220> FEATURE:
<221> NAME/KEY: SITE
<222> LOCATION: (11)
<223> OTHER INFORMATION: THIS C-TERMINAL AMINO ACID ENDS WITH AN NH2.
<223> OTHER INFORMATION: Description of Artificial Sequence:ANALOG OF
      BOMBESIN.

<400> SEQUENCE: 3

Gly Asp Gly Gln Trp Ala Val Gly His Leu Met
  1               5                  10

<210> SEQ ID NO 4
<211> LENGTH: 8
<212> TYPE: PRT
<213> ORGANISM: Artificial Sequence
<220> FEATURE:
<221> NAME/KEY: SITE
<222> LOCATION: (8)
<223> OTHER INFORMATION: THIS C-TERMINAL RESIDUE ENDS WITH NH2.
```

```
<223> OTHER INFORMATION: Description of Artificial Sequence:ANALOG OF
      CHOLECYSTOKININ

<400> SEQUENCE: 4

Asp Ty

```
<220> FEATURE:
<223> OTHER INFORMATION: Description of Artificial Sequence:Octreotate
<221> NAME/KEY: SITE
<222> LOCATION: (1)
<223> OTHER INFORMATION: This is D-phenylalanine
<221> NAME/KEY: DISULFID
<222> LOCATION: (2)..(7)
<221> NAME/KEY: SITE
<222> LOCATION: (4)
<223> OTHER INFORMATION: This is D-tryptophan

<400> SEQUENCE: 8

Phe Cys Tyr Trp Lys Thr Cys Thr
 1               5
```

INDOCYANINE DYES

This is a Divisional Application of U.S. application Ser. No. 09/484,323 filed on Jan. 18, 2000.

FIELD OF INVENTION

This invention relates generally to novel cyanine and indocyanine dyes for use in imaging, diagnosis and therapy. Particularly, this invention relates to compositions of cyanine and indocyanine dyes wherein novel carbocyclic and heterocyclic moieties are incorporated into the polyene portion of the dye molecules.

BACKGROUND OF THE INVENTION

Several dyes that absorb and emit light in the visible and near-infrared region of electromagnetic spectrum are currently being used for various biomedical applications due to their biocompatibility, high molar absorptivity, or high fluorescence quantum yields. The high sensitivity of the optical modality in conjunction with dyes as contrast agents parallels that of nuclear medicine and permits visualization of organs and tissues without the undesirable effect of ionizing radiation. Cyanine dyes with intense absorption and emission in the near-infrared (NIR) region are particularly useful because biological tissues are optically transparent in this region (B. C. Wilson, Optical properties of tissues. *Encyclopedia of Human Biology*, 1991, 5, 587–597). For example, indocyanine green, which absorbs and emits in the NIR region has been used for monitoring cardiac output, hepatic functions, and liver blood flow (Y-L. He, H. Tanigami, H. Ueyama, T. Mashimo, and I. Yoshiya, Measurement of blood volume using indocyanine green measured with pulse-spectrometry: Its reproducibility and reliability. *Critical Care Medicine*, 1998, 26(8), 1446–1451; J. Caesar, S. Shaldon, L. Chiandussi, et al., The use of Indocyanine green in the measurement of hepatic blood flow and as a test of hepatic function. *Clin. Sci.* 1961, 21, 43–57) and its functionalized derivatives have been used to conjugate biomolecules for diagnostic purposes (R. B. Mujumdar, L. A. Ernst, S. R. Mujumdar, et al., Cyanine dye labeling reagents: Sulfoindocyanine succinimidyl esters. *Bioconjugate Chemistry*, 1993, 4(2), 105–111; Linda G. Lee and Sam L. Woo. "N-Heteroaromatic ion and iminium ion substituted cyanine dyes for use as fluorescent labels", U.S. Pat. No. 5,453,505; Eric Hohenschuh, et al. "Light imaging contrast agents", WO 98/48846; Jonathan Turner, et al. "Optical diagnostic agents for the diagnosis of neurodegenerative diseases by means of near infra-red radiation", WO 98/22146; Kai Licha, et al. "In-vivo diagnostic process by near infrared radiation", WO 96/17628; Robert A. Snow, et al., Compounds, WO 98/48838).

A major drawback in the use of cyanine dye derivatives is the potential for hepatobilliary toxicity resulting from the rapid clearance of these dyes by the liver (G. R. Cherrick, S. W. Stein, C. M. Leevy, et al., Indocyanine green: Observations on its physical properties, plasma decay, and hepatic extraction. *J. Clinical Investigation*, 1960, 39, 592–600). This is associated with the tendency of cyanine dyes to form aggregates in solution which could be taken up by Kupffer cells in the liver. Various attempts to obviate this problem have not been very successful. Typically, hydrophilic peptides, polyethyleneglycol or oligosaccharide conjugates have been used but these resulted in long-circulating products which are eventually cleared by the liver. Another major difficulty with current cyanine and indocyanine dye systems is that they offer a limited scope in the ability to induce large changes in the absorption and emission properties of these dyes. Attempts have been made to incorporate various heteroatoms and cyclic moieties into the polyene chain of these dyes (L. Strekowski, M. Lipowska, and G. Patonay, Substitution reactions of a nucleofugal group in hetamethine cyanine dyes. *J. Org. Chem.*, 1992, 57, 4578–4580; N. Narayanan, and G. Patonay, A new method for the synthesis of heptamethine cyanine dyes: Synthesis of new near infrared fluorescent labels. *J. Org. Chem.*, 1995, 60, 2391–2395; E. Fung and R. Rajagopalan, Monocyclic functional dyes for contrast enhancement in optical imaging, U.S. Pat. No. 5,732,104; R. Rajagopalan and E. Fung, Delta$^{1,6}$ bicyclo[4,4,0] functional dyes for contrast enhancement in optical imaging, U.S. Pat. No. 5,672,333; R. Rajagopalan and E. Fung, Tricyclic functional dyes for contrast enhancement in optical imaging, U.S. Pat. No. 5,709,845) but the resulting dye systems do not show large differences in absorption and emission maxima, especially beyond 830 nm where photacoustic diagnostic applications are very sensitive. They also possess prominent hydrophobic core which enhances liver uptake. Further, most cyanine dyes do not have the capacity to form dendrimers which are useful in biomedical applications.

Therefore, there is a need to design novel dyes that could prevent dye aggregation in solution, predisposed to form dendrimers, capable of absorbing or emitting beyond 800 nm, possess desirable photophysical properties, and endowed with tissue-specific targeting capability.

The publications and other materials used herein to support the background of the invention or provide additional details respecting the practice, are incorporated by reference.

SUMMARY OF THE INVENTION

The present invention relates particularly to the novel composition comprising cyanine dyes of general formula 1

Formula 1

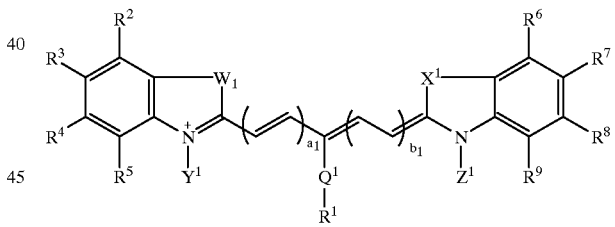

wherein $a_1$ and $b_1$ vary from 0 to 5; $W^1$ and $X^1$ may be the same or different and are selected from the group consisting of —$CR^{10}R^{11}$, —O—, —$NR^{12}$, —S—, and —Se; $Q^1$ is a single bond or is selected from the group consisting of —O—, —S—, —Se—, and —$NR^{13}$; $Y^1$ and $Z^1$ may be the same or different and are selected from the group consisting of —$(CH_2)_c$—$CO_2H$, —$CH_2$—$(CH_2$—O—$CH_2)_d$—$CH_2$—$CO_2H$, —$(CH_2)_8$—$NH_2$, —$CH_2$—$(CH_2$—O—$CH_2)_f$—$CH_2$—$NH_2$, —$(CH_2)_g$—$N(R^{14})$—$(CH_2)_h$—$CO_2H$, and —$(CH_2)_i$—$N(R^{15})$—$CH_2$—$(CH_2$—O—$CH_2)_j$—$CH_2$—$CO_2H$; $R^1$ and $R^{10}$ to $R^{15}$ may be same or different and are selected from the group consisting of -hydrogen, C1–C10 alkyl, C1–C10 aryl, C1–C10 alkoxyl, C1–C10 polyalkoxyalkyl, —$CH_2(CH_2$—O—$CH_2)_c$—$CH_2$—OH, C1–C20 polyhydroxyalkyl, C1–C10 polyhydroxyaryl, —$(CH_2)_d$—$CO_2H$, —$CH_2$—$(CH_2$—O—$CH_2)_e$—$CH_2$—$CO_2H$, —$(CH_2)_f$—$NH_2$, and —$CH_2$—$(CH_2$—O—$CH_2)_g$—$CH_2$—$NH_2$; c, e, g, h, and i vary from 1 to 10; d, f and j vary from 1 to 100; and $R^2$ to $R^9$ may be the same or different and are selected from the group consisting of hydrogen, C1–C10 alkyl, C1–C10 aryl, hydroxyl, C1–C10 polyhydroxyalkyl, C1–C10 alkoxyl, amino, C1–C10 aminoalkyl, cyano, nitro and halogen.

The present invention also relates to the novel composition comprising indocyanine dyes of general formula 2

Formula 2

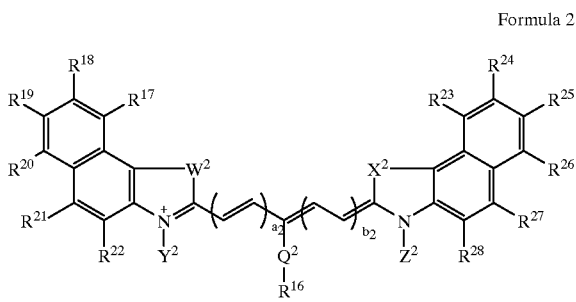

wherein $a_2$ and $b_2$ are defined in the same manner as $a_1$ and $b_1$; $W^2$ and $X^2$ are defined in the same manner $W^1$ and $X^1$; $Q^2$ is defined in the same manner as $Q^1$; $R^{16}$ and $R^{10}$ to $R^{15}$ are defined in the same manner as $R^1$ and $R^{10}$ to $R^{15}$; $Y^2$ is defined in the same manner as $Y^1$; $Z^2$ is defined in the same manner as $Z^1$; and $R^{17}$ to $R^{28}$ are defined in the same manner as $R^2$ to $R^9$.

The present invention also relates to the novel composition comprising cyanine dyes of general formula 3

Formula 3

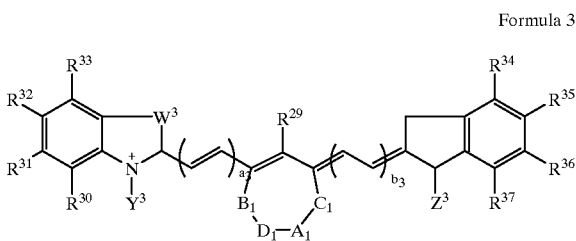

wherein $a_3$ and $b_3$ are defined in the same manner as $a_1$ and $b_1$; $W^3$ and $X^3$ are defined in the same manner $W^1$ and $X^1$; $Y^3$ is defined in the same manner as $Y^1$; $Z^3$ is defined in the same manner as $Z^1$; $A_1$ is a single or a double bond; if $A_1$ is a single bond, then $B_1$ and $C_1$ may the same or different and are selected from the group consisting of —O—, —S—, —Se—, —P—, and —NR$^{38}$ and $D_1$ is selected from the group consisting of —CR$^{39}$R$^{40}$, and —C=O; if $A_1$ is a double bond, then $B_1$ is selected from the group consisting of —O—, —S—, —Se—, —P— and —NR$^{38}$, $C_1$ is nitrogen or —CR$^{41}$, and $D_1$ is —CR$^{42}$; $R^{29}$ to $R^{37}$ are selected from the group consisting of hydrogen, C1–C10 alkyl, C1–C10 aryl, hydroxyl, hydrophilic peptide, C1–C10 polyhydroxyalkyl, C1–C10 alkoxyl, cyano, nitro, halogen and —NR$^{43}$R$^{44}$; $R^{38}$ to $R^{42}$ may be same or different and are selected from the group consisting of -hydrogen, C1–C10 alkyl, C1–C10 aryl, C1–C10 alkoxyl, C1–C10 polyalkoxyalkyl, —CH$_2$(CH$_2$—O—CH$_2$)$_c$—CH$_2$—OH, C1–C20 polyhydroxyalkyl, C1–C10 polyhydroxyaryl, —(CH$_2$)$_d$—CO$_2$H, —CH$_2$—(CH$_2$—O—CH$_2$)$_e$—CH$_2$—CO$_2$H, —(CH$_2$)$_f$—NH$_2$, and —CH$_2$—(CH$_2$—O—CH$_2$)$_g$—CH$_2$—NH$_2$; c, e, g, h, and i vary from 1 to 10; d, f and j vary from 1 to 100; $R^{43}$ and $R^{44}$ may be the same or different and are selected from the group consisting of hydrogen, C1–C10 alkyl, C1–C10 aryl, or may together form a 5, 6, or 7 membered carbocyclic ring or a 5, 6, or 7 membered heterocyclic ring optionally containing one or more oxygen, nitrogen, or a sulfur atom.

The present invention also relates to the novel composition comprising indocyanine dyes of general formula 4 wherein $a_4$ and $b_4$ are defined in the same manner as $a_1$ and $b_1$; $W^4$ and $X^4$ are defined in the same manner as $W^1$ and $X^1$; $Y^4$ is defined in the same manner as $Y^1$; $Z^4$ is defined in the same manner as $Z^1$; $A_2$ is defined in the same manner as $A_1$; $B_2$, $C_2$, and $D_2$ are defined in the same manner as $B_1$, $C_1$, and $D_1$; and $R^{45}$ to $R^{57}$ are defined in the same manner as $R^{29}$ to $R^{37}$.

Formula 4

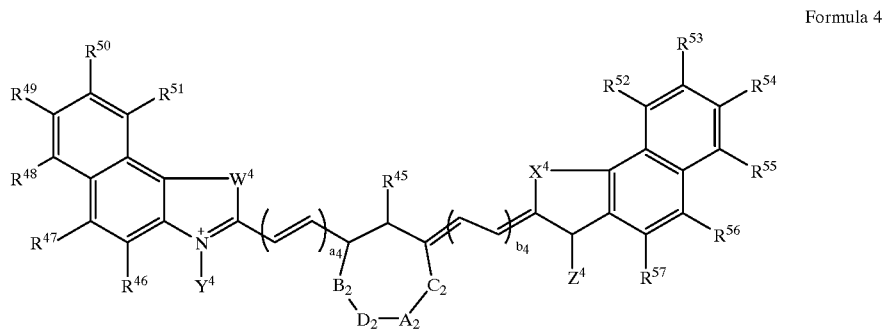

The present invention also relates to the novel composition comprising cyanine dyes of general formula 5

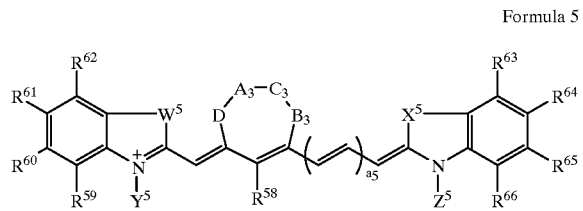

Formula 5 wherein $a_5$ is defined in the same manner as $a_1$; $W^5$ and $X^5$ are defined in the same manner $W^1$ and $X^1$; $Y^5$ is defined in the same manner as $Y^1$; $Z^5$ is defined in the same manner as $Z^1$; $A_3$ is defined in the same manner as $A_1$; $B_3$, $C_3$, and $D_3$ are defined in the same manner as $B_1$, $C_1$, and $D_1$; and $R^{58}$ to $R^{66}$ are defined in the same manner as $R^{29}$ to $R^{37}$.

The present invention also relates to the novel composition comprising cyanine dyes of general formula 6

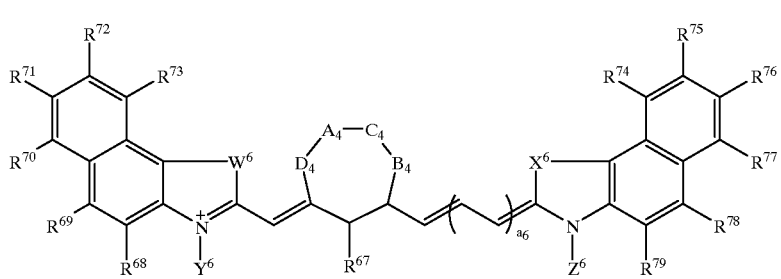

Formula 6 wherein $a_6$ is defined in the same manner as $a_1$; $W^6$ and $X^6$ are defined in the same manner as $W^1$ and $X^1$; $Y^6$ is defined in the same manner as $Y^1$; $Z^6$ is defined in the same manner as $Z^1$; $A_4$ is defined in the same manner as $A_1$; $B_4$, $C_4$, and $D_4$ are defined in the same manner as $B_1$, $C_1$, and $D_1$; and $R^{67}$ to $R^{79}$ are defined in the same manner as $R^{29}$ to $R^{37}$.

This invention is also related to the method of conjugating the dyes of this invention to peptides or biomolecules by solid phase synthesis.

This invention is also related to the method of preventing fluorescence quenching. It is known that cyanine dyes generally form aggregates in aqueous media leading to fluorescence quenching. We observed that in instances where the presence of hydrophobic core in the dyes lead fluorescence quenching, the addition of a biocompatible organic solvent such as 1–50% dimethylsulfoxide (DMSO) restored the fluorescence by preventing aggregation and allowed in vivo organ visualization.

DETAILED DESCRIPTION OF THE INVENTION

The novel compositions of the present invention comprising dyes of formulas 1 to 6 offer significant advantages over those currently described in the art. As illustrated in FIGS. 1–6, these dyes are designed to prevent aggregation in solution by preventing intramolecular and intermolecular ordered hydrophobic interactions. They also have multiple attachment sites proximal to the dye chromophore for ease of forming dendrimers. The presence of rigid and extended chromophore backbone enhances fluorescence quantum yield and extends the maximum absorption beyond 800 nm. Conjugation of biomolecules to these dyes are readily achievable. They are useful in various biomedical applications including, but not limited to, tomographic imaging of organs; monitoring of organ functions; coronary angiography; fluorescence endoscopy; detection, imaging, and therapy of tumors; laser guided surgery, photoacoustic and sonofluorescence methods; and the like. Specific embodiments to accomplish some of the aforementioned biomedical applications are given below.

In one embodiment of the invention, the dyes of the invention are useful for optical tomographic, endoscopic, photoacoustic and sonofluoresence applications for the detection and treatment of tumors and other abnormalities.

In another aspect of the invention, the dyes of the invention are useful for localized therapy.

In yet another aspect of the invention, the dyes of the invention are useful for the detection of the presence of tumors and other abnormalities by monitoring the blood clearance profile of the dyes.

In a further embodiment of the invention, the dyes are useful for laser assisted guided surgery for the detection of micrometastases of tumors upon laparoscopy.

In yet another aspect of the invention, the dye bioconjugates of the dyes of this invention are useful diagnosis of atherosclerotic plaques and blood clots.

Figure 4:
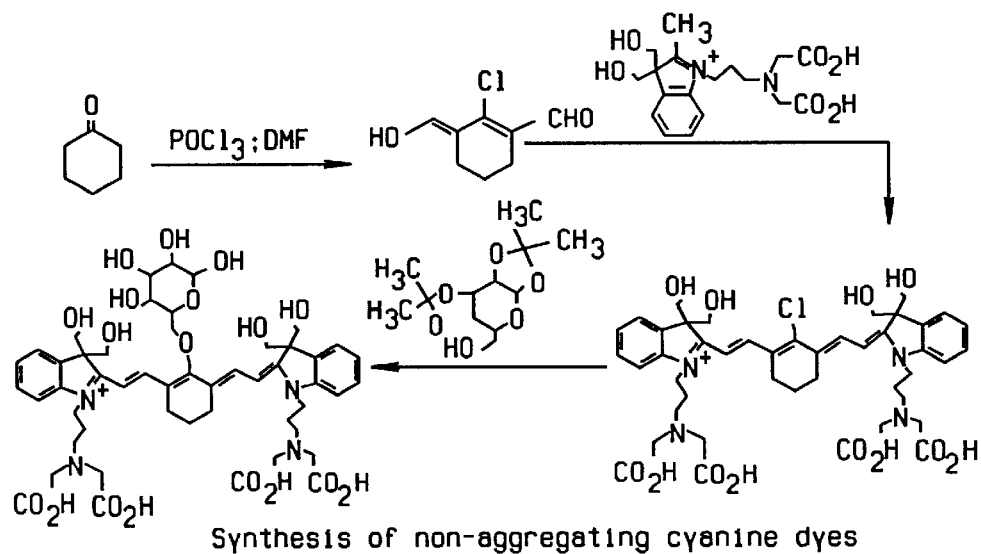
FIG. 4 shows the reactions in the synthesis of non-aggregating cyanine dyes of this invention.
Figure 5:
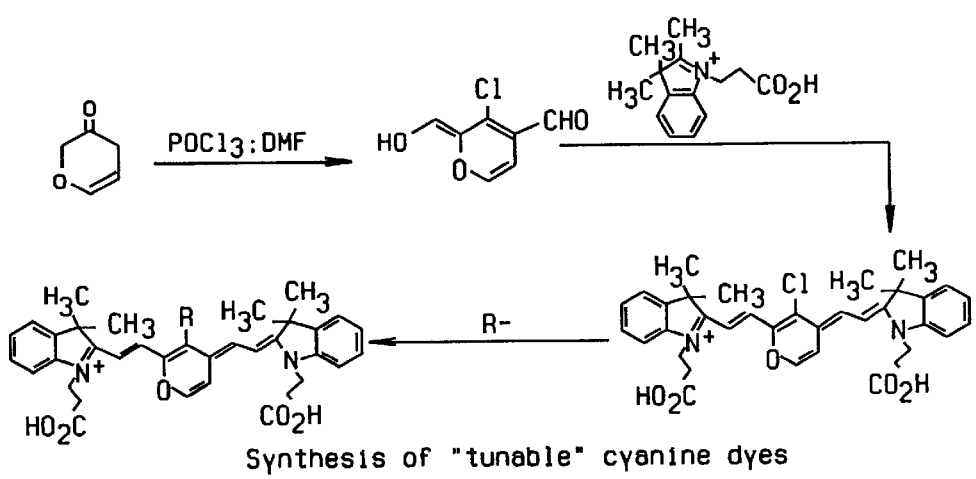
FIG. 5 shows the reactions in the synthesis of "tunable" cyanine dyes of this invention.
Figure 6:
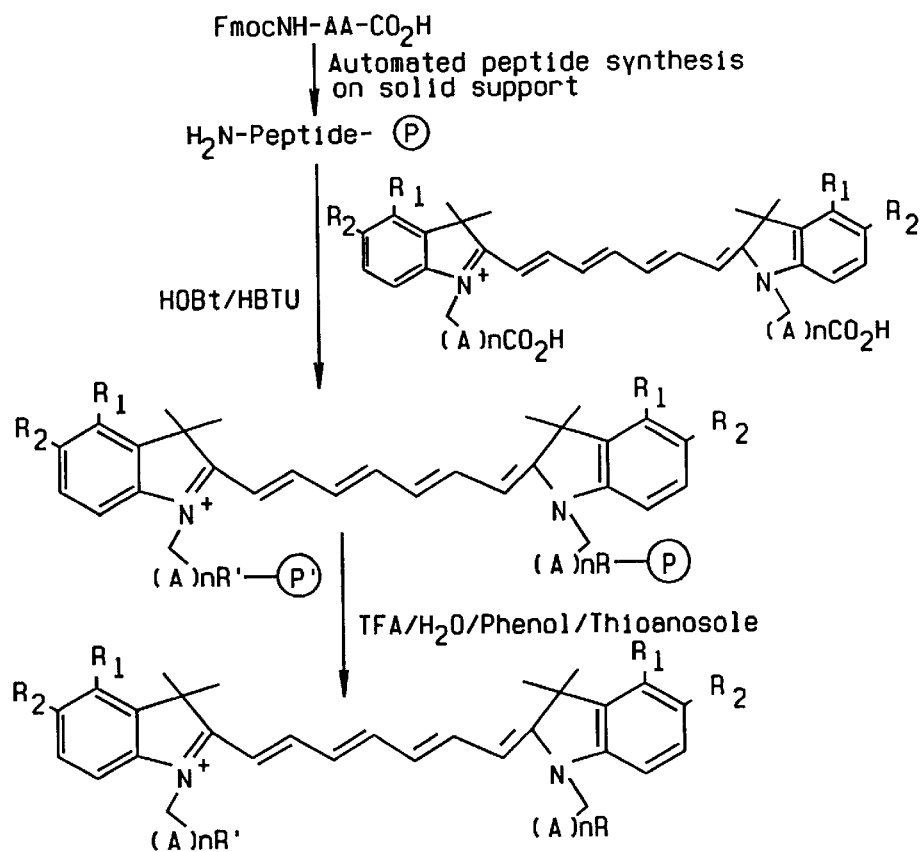
FIG. 6 shows the reactions in a representative scheme for the preparation of bioconjugates of this invention.

The novel dyes of the present invention are prepared according the methods well known in the art and are shown in FIGS. 1–5 and their use in the synthesis of bioconjugates is shown in FIG. 6.

In a preferred embodiment, the dyes according to the present invention have the general Formula 1 wherein $a_1$ and $b_1$ vary from 0 to 3; $Q^1$ is a single bond; $R^1$ to $R^9$ are hydrogens; $W^1$ and $X^1$ may be the same or different and are selected from the group consisting of —C(CH$_3$)$_2$, C((CH$_2$)$_{zz}$OH)CH$_3$, C((CH$_2$)$_{zz}$OH)$_2$, C((CH$_2$)$_{zz}$CO$_2$H)CH$_3$, C((CH$_2$)$_{zz}$CO$_2$H)$_2$, C((CH$_2$)$_{zz}$NH$_2$)CH$_3$, C((CH$_2$)$_{zz}$NH$_2$)$_2$, C((CH$_2$)$_{zz}$NR$_{pp}$R$_{pz}$)CH$_3$ and C((CH$_2$)$_{zz}$NR$_{pp}$R$_{pz}$)$_2$; $Y^1$ and $Z^1$ may be the same or different and are selected from the group consisting of —(CH$_2$)$_c$—CO$_2$H, —CH$_2$—(CH$_2$—O—CH$_2$)$_d$ —CH$_2$—CO$_2$H, —(CH$_2$)$_g$—N(R$^{14}$)—(CH$_2$)$_h$—

$CO_2H$, and $-(CH_2)_i-N(R^{15})-CH_2-(CH_2-O-CH_2)_j-CH_2-CO_2H$; $R_{pp}$ and $R_{pz}$ may be the same or different and are selected from the group consisting of $-(CH_2)_c-CO_2H$, $-CH_2-(CH_2-O-CH_2)_d-CH_2-CO_2H$, $-(CH_2)_g-N(R^{14})-(CH_2)_h-CO_2H$, and $-(CH_2)_i-N(R^{15})-CH_2-(CH_2-O-CH_2)_j-CH_2-CO_2H$; $R^{14}$ and $R^{15}$ may be same or different and are selected from the group consisting of -hydrogen, C1–C10 alkyl, C1–C10 aryl, C1–C10 alkoxyl, C1–C10 polyalkoxyalkyl, $-CH_2(CH_2-O-CH_2)_c-CH_2-OH$, C1–C20 polyhydroxyalkyl, C1–C10 polyhydroxyaryl, $-(CH_2)_d-CO_2H$, $-CH_2-(CH_2-O-CH_2)_e-CH_2-CO_2H$, $-(CH_2)_f-NH_2$, and $-CH_2-(CH_2-O-CH_2)_g-CH_2-NH_2$; c, e, g, h, i, and zz vary from 1 to 5; and d, f and j vary from 1 to 100.

In another preferred embodiment, the dyes according to the present invention have the general Formula 2 wherein $a_2$ and $b_2$ vary from 0 to 3; $Q^2$ is a single bond; $R^{16}$ to $R^{28}$ are hydrogens; $W^2$ and $X^2$ may be the same or different and are selected from the group consisting of $-C(CH_3)_2$, $C((CH_2)_{zz}OH)CH_3$, $C((CH_2)_{zz}OH)_2$, $C((CH_2)_{zz}CO_2H)CH_3$, $C((CH_2)_{zz}CO_2H)_2$, $C((CH_2)_{zz}NH_2)CH_3$, $C((CH_2)_{zz}NH_2)_2$, $C((CH_2)_{zz}NR_{pp}R_{pz})CH_3$ and $C((CH_2)_{zz}NR_{pp}R_{pz})_2$; $Y^2$ and $Z^2$ may be the same or different and are selected from the group consisting of $-(CH_2)_c-CO_2H$, $-CH_2-(CH_2-O-CH_2)_d-CH_2-CO_2H$, $-(CH_2)_g N(R^{14})-(CH_2)_h-CO_2H$, and $-(CH_2)_i-N(R^{15})-CH_2-(CH_2-O-CH_2)_j-CH_2-CO_2H$; $R_{pp}$ and $R_{pz}$ may be the same or different and are selected from the group consisting of $-(CH_2)_c-CO_2H$, $-CH_2-(CH_2-O-CH_2)_d-CH_2-CO_2H$, $-(CH_2)_g-N(R^{14})-(CH_2)_h-CO_2H$, and $-(CH_2)_i-N(R^{15})-CH_2-(CH_2-O-CH_2)_j-CH_2-CO_2H$; $R^{14}$ and $R^{15}$ may be same or different and are selected from the group consisting of -hydrogen, C1–C10 alkyl, C1–C10 aryl, C1–C10 alkoxyl, C1–C10 polyalkoxyalkyl, $-CH_2(CH_2-O-CH_2)_c-CH_2-OH$, C1–C20 polyhydroxyalkyl, C1–C10 polyhydroxyaryl, $-(CH_2)_d-CO_2H$, $-CH_2-(CH_2-O-CH_2)_e-CH_2-CO_2H$, $-(CH_2)_f-NH_2$, and $-CH_2-(CH_2-O-CH_2)_g-CH_2-NH_2$; c, e, g, h, i, and zz vary from 1 to 5; and d, f and j vary from 1 to 100.

In another preferred embodiment, the dyes according to the present invention have the general Formula 3 wherein $a_3$ and $b_3$ vary from 0 to 3; $A_1$ is a single bond; $B_1$ is selected from the group consisting of $-O-$, $-S-$, and $-NR^{38}$; $C_1$ is $-CH_2$ or $-C=O$; $D_1$ is selected from the group consisting of $-O-$, $-S-$, and $-NR^{38}$; $R^{29}$ is a hydrogen, a halogen atom, a saccharide or a hydrophilic peptide; $R^{30}$ to $R^{37}$ are hydrogens; $R^{38}$ is selected from the group consisting of -hydrogen, C1–C10 alkyl, C1–C10 aryl, C1–C10 alkoxyl, C1–C10 polyalkoxyalkyl, $-CH_2(CH_2-O-CH_2)_c-CH_2-OH$, C1–C20 polyhydroxyalkyl, C1–C10 polyhydroxyaryl, $-(CH_2)_d-CO_2H$, $-CH_2-(CH_2-O-CH_2)_e-CH_2-CO_2H$, $-(CH_2)_f-NH_2$, and $-CH_2-(CH_2-O-CH_2)_g-CH_2-NH_2$; $W^3$ and $X^3$ may be the same or different and are selected from the group consisting of $-C(CH_3)_2$, $C((CH_2)_{zz}OH)CH_3$, $C((CH_2)_{zz}OH)_2$, $C((CH_2)_{zz}CO_2H)CH_3$, $C((CH_2)_{zz}CO_2H)_2$, $C((CH_2)_{zz}NH_2)CH_3$, $C((CH_2)_{zz}NH_2)_2$, $C((CH_2)_{zz}NR_{pp}R_{pz})CH_3$ and $C((CH_2)_{zz}NR_{pp}R_{pz})_2$; $Y^3$ and $Z^3$ may be different and are selected from the group consisting of $-(CH_2)_c-CO_2H$, $-CH_2-(CH_2-O-CH_2)_d-CH_2-CO_2H$, $-(CH_2)_g-N(R^{14})-(CH_2)_h-CO_2H$, and $-(CH_2)_i-N(R^{15})-CH_2-(CH_2-O-CH_2)_j-CH_2-CO_2H$; $R_{pp}$ and $R_{pz}$ may be the same or different and are selected from the group consisting of $-(CH_2)_c-CO_2H$, $-CH_2-(CH_2-O-CH_2)_d-CH_2-CO_2H$, $-(CH_2)_g-N(R^{14})-(CH_2)_h-CO_2H$, and $-(CH_2)_i-N(R^{15})-CH_2-(CH_2-O-CH_2)_j-CH_2-CO_2H$; $R^{14}$ and $R^{15}$ may be same or different an are selected from the group consisting of -hydrogen, C1–C10 alkyl, C1–C10 aryl, C1–C10 alkoxyl, C1–C10 polyalkoxyalkyl, $-CH_2(CH_2-O-CH_2)_c-CH_2-OH$, C1–C20 polyhydroxyalkyl, C1–C10 polyhydroxyaryl, $-(CH_2)_d-CO_2H$, $-CH_2-(CH_2-O-CH_2)_e-CH_2-CO_2H$, $-(CH_2)_f-NH_2$, and $-CH_2-(CH_2-O-CH_2)_g-CH_2-NH_2$; c, e, g, h, i, and zz vary from 1 to 5; and d, f and j vary from 1 to 100.

In another preferred embodiment, the dyes according to the present invention have the general Formula 4 wherein $a_4$ and $b_4$ vary from 0 to 3; $A_2$ is a single or double bond; $B_2$ is selected from the group consisting of $-O-$, $-S-$, or $-NR^{38}$; $C_2$ is $-CH_2$ or $-C=O$; $D_2$ is selected from the group consisting of $-O-$, $-S-$ and $-NR^{38}$; $R^{38}$ is selected from the group consisting of -hydrogen, C1–C10 alkyl, C1–C10 aryl, C1–C10 alkoxyl, C1–C10 polyalkoxyalkyl, $-CH_2(CH_2-O-CH_2)_c-CH_2-OH$, C1–C20 polyhydroxyalkyl, C1–C10 polyhydroxyaryl, $-(CH_2)_d-CO_2H$, $-CH_2-(CH_2-O-CH_2)_e-CH_2-CO_2H$, $-(CH_2)_f-NH_2$, and $-CH_2-(CH_2-O-CH_2)_g-CH_2-NH_2$; $R^{45}$ is a hydrogen, a halogen atom, a saccharide or a hydrophilic peptide; $R^{46}$ to $R^{57}$ are hydrogens; $W^4$ and $X^4$ may be the same or different and are selected from the group consisting of $-C(CH_3)_2$, $C((CH_2)_{zz}OH)CH_3$, $C((CH_2)_{zz}OH)_2$, $C((CH_2)_{zz}CO_2H)CH_3$, $C((CH_2)_{zz}CO_2H)_2$, $C((CH_2)_{zz}NH_2)CH_3$, $C((CH_2)_{zz}NH_2)_2$, $C((CH_2)_{zz}NR_{pp}R_{pz})CH_3$ and $C((CH_2)_{zz}NR_{pp}R_{pz})_2$; $Y^4$ and $Z^4$ may be the same or different and are selected from the group consisting of $-(CH_2)_c-CO_2H$, $-CH_2-(CH_2-O-CH_2)_d-CH_2-CO_2H$, $-(CH_2)_g-N(R^{14})-(CH_2)_h-CO_2H$, and $-(CH_2)_i-N(R^{15})-CH_2-(CH_2-O-CH_2)_j-CH_2-CO_2H$; $R_{pp}$ and $R_{pz}$ are the same or different and are selected from $-(CH_2)_c-CO_2H$, $-CH_2-(CH_2-O-CH_2)_d-CH_2-CO_2H$, $-(CH_2)_g-N(R^{14})-(CH_2)_h-CO_2H$, and $-(CH_2)_i-N(R^{15})-CH_2-(CH_2-O-CH_2)_j-CH_2-CO_2H$; $R^{14}$ and $R^{15}$ may be the same or different and are selected from the group consisting of -hydrogen, C1–C10 alkyl, C1–C10 aryl, C1–C10 alkoxyl, C1–C10 polyalkoxyalkyl, $-CH_2(CH_2-O-CH_2)_c-CH_2-OH$, C1–C20 polyhydroxyalkyl, C1–C10 polyhydroxyaryl, $-(CH_2)_d-CO_2H$, $-CH_2-(CH_2-O-CH_2)_e-CH_2-CO_2H$, $-(CH_2)_f-NH_2$, and $-CH_2-(CH_2-O-CH_2)_g-CH_2-NH_2$; c, e, g, h, i, and zz vary from 1 to 5; and d, f and j vary from 1 to 100.

In another preferred embodiment, the dyes according to the present invention have the general Formula 5 wherein $a_5$ varies from 0 to 3; $A_3$ is a single or double bond; $B_3$ is selected from the group consisting of $-O-$, $-S-$ and $-NR^{38}$; $C_3$ is $-CH_2$ or $-C=O$; $D_3$ is selected from the group consisting of $-O-$, $-S-$ and $-NR^{38}$; $R^{38}$ is selected from the group consisting of -hydrogen, C1–C10 alkyl, C1–C10 aryl, C1–C10 alkoxyl, C1–C10 polyalkoxyalkyl, $-CH_2(CH_2-O-CH_2)_c-CH_2-OH$, C1–C20 polyhydroxyalkyl, C1–C10 polyhydroxyaryl, $-(CH_2)_d-CO_2H$, $-CH_2-(CH_2-O-CH_2)_e-CH_2-CO_2H$, $-(CH_2)_f-NH_2$, and $-CH_2-(CH_2-O-CH_2)_g-CH_2-NH_2$; $R^{58}$ is a hydrogen, a halogen atom, a saccharide or a hydrophilic peptide; $R^{59}$ to $R^{66}$ are hydrogens; $W^5$ and $X^5$ may be the same or different and are selected from the group consisting of $-C(CH_3)_2$, $C((CH_2)_{zz}OH)CH_3$, $C((CH_2)_{zz}OH)_2$, $C((CH_2)_{zz}CO_2H)CH_3$, $C((CH_2)_{zz}CO_2H)_2$, $C((CH_2)_{zz}NH_2)CH_3$, $C((CH_2)_{zz}NH_2)_2$, $C((CH_2)_{zz}NR_{pp}R_{pz})CH_3$ and $C((CH_2)_{zz}NR_{pp}R_{pz})_2$; $Y^5$ and $Z^5$ may be the same or different and are selected from the group consisting of $-(CH_2)_c-CO_2H$, $-CH_2-(CH_2-O-CH_2)_d-CH_2-CO_2H$, $-(CH_2)_g-N(R^{14})-(CH_2)_h-CO_2H$, and $-(CH_2)_i-N(R^{15})-CH_2-(CH_2-O-CH_2)_j-CH_2-CO_2H$; $R_{pp}$ and $R_{pz}$ are the same or different and are selected from —$(CH_2)_c$—$CO_2H$, —$CH_2$—$(CH_2$—O—$CH_2)_d$—$CH_2$—$CO_2H$, —$(CH_2)_g$—$N(R^{14})$—$(CH_2)_h$—$CO_2H$, and —$(CH_2)_i$—$N(R^{15})$—$CH_2$—$(CH_2$—O—$CH_2)_j$—$CH_2$—$CO_2H$; $R^{14}$ and $R^{15}$ may be the same or different and are selected from the group consisting of -hydrogen, C1–C10 alkyl, C1–C10 aryl, C1–C10 alkoxyl, C1–C10 polyalkoxyalkyl, —$CH_2$ ($CH_2$—O—$CH_2)_c$—$CH_2$—OH, C1–C20 polyhydroxyalkyl, C1–C10 polyhydroxyaryl, —$(CH_2)_d$—$CO_2H$, —$CH_2$—($CH_2$—O—$CH_2)_e$—$CH_2$—$CO_2H$, —$(CH_2)_f$—$NH_2$, and —$CH_2$—($CH_2$—O—$CH_2)_g$—$CH_2$—$NH_2$; c, e, g, h, i, and zz vary from 1 to 5; and d, f and j vary from 1 to 100.

In another preferred embodiment, the dyes according to the present invention have the general Formula 6 wherein $a_6$ varies from 0 to 3; $A_4$ is a single or double bond; $B_4$ is selected from the group consisting of —O—, —S— and —$NR^{38}$; $C_4$ is —$CH_2$ or —C=O; $D_4$ is selected from the group consisting of —O—, —S— and —$NR^{38}$; $R^{38}$ is selected from the group consisting of -hydrogen, C1–C10 alkyl, C1–C10 aryl, C1–C10 alkoxyl, C1–C10 polyalkoxyalkyl, —$CH_2(CH_2$—O—$CH_2)_c$—$CH_2$—OH, C1–C20 polyhydroxyalkyl, C1–C10 polyhydroxyaryl, —$(CH_2)_d$—$CO_2H$, —$CH_2$—($CH_2$—O—$CH_2)_e$—$CH_2$—$CO_2H$, —$(CH_2)_f$—$NH_2$, and —$CH_2$—($CH_2$—O—$CH_2)_g$—$CH_2$—$NH_2$; $R^{67}$ is a hydrogen, a halogen atom, a saccharide or a hydrophilic peptide; $R^{68}$ to $R^{79}$ are hydrogens; $W^6$ and $X^6$ may be the same of different and are selected from the group consisting of —$C(CH_3)_2$, $C((CH_2)_{zz}OH)CH_3$, $C((CH_2)_{zz}OH)_2$, $C((CH_2)_{zz}CO_2H)CH_3$, $C((CH_2)_{zz}CO_2H)_2$, $C((CH_2)_{zz}NH_2)CH_3$, $C((CH_2)_{zz}NH_2)_2$, $C((CH_2)_{zz}NR_{pp}R_{pz})CH_3$ and $C((CH_2)_{zz}NR_{pp}R_{pz})_2$; $Y^6$ and $Z^6$ may be the same or different and are selected from the group consisting of —$(CH_2)_c$—$CO_2H$, —$CH_2$—($CH_2$—O—$CH_2)_d$—$CH_2$—$CO_2H$, —$(CH_2)_g$—$N(R^{14})$—$(CH_2)_h$—$CO_2H$ and —$(CH_2)_i$—$N(R^{15})$—$CH_2$—($CH_2$—O—$CH_2)_j$—$CH_2$—$CO_2H$; $R_{pp}$ and $R_{pz}$ are the same or different and are selected from the group consisting of —$(CH_2)_c$—$CO_2H$, —$CH_2$—($CH_2$—O—$CH_2)_d$—$CH_2$—$CO_2H$, —$(CH_2)_g$—$N(R^{14})$—$(CH_2)_h$—$CO_2H$ and —$(CH_2)_i$—$N(R^{15})$—$CH_2$—($CH_2$—O—$CH_2)_j$—$CH_2$—$CO_2H$; $R^{14}$ and $R^{15}$ may be the same different and are selected from the group consisting of -hydrogen, C1–C10 alkyl, C1–C10 aryl, C1–C10 alkoxyl, C1–C10 polyalkoxyalkyl, —$CH_2(CH_2$—O—$CH_2)_c$—$CH_2$—OH, C1–C20 polyhydroxyalkyl, C1–C10 polyhydroxyaryl, —$(CH_2)_d$—$CO_2H$, —$CH_2$—($CH_2$—O—$CH_2)_e$—$CH_2$—$CO_2H$, —$(CH_2)_f$—$NH_2$, and —$CH_2$—($CH_2$—O—$CH_2)_g$—$CH_2$—$NH_2$; c, e, g, h, i, and zz vary from 1 to 5; and d, f and j vary from 1 to 100.

The compositions of the invention can be formulated into diagnostic compositions for enteral or parenteral administration. These compositions contain an effective amount of the dye along with conventional pharmaceutical carriers and excipients appropriate for the type of administration contemplated. For example, parenteral formulations advantageously contain a sterile aqueous solution or suspension of dye according to this invention. Parenteral compositions may be injected directly or mixed with a large volume parenteral composition for systemic administration. Such solutions also may contain pharmaceutically acceptable buffers and, optionally, electrolytes such as sodium chloride.

Formulations for enteral administration may vary widely, as is well known in the art. In general, such formulations are liquids which include an effective amount of the dye in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement. Such doses may vary widely, depending upon the particular dye employed, the organs or tissues which are the subject of the imaging procedure, the imaging equipment being used, and the like.

The diagnostic compositions of the invention are used in the conventional manner. The compositions may be administered to a patient, typically a warm-blooded animal, either systemically or locally to the organ or tissue to be imaged, and the patient then subjected to the imaging procedure.

A combination of the above represents an important approach to the synthesis and use of novel cyanine and indocyanine dyes with a variety of photophysical and chemical properties. The dyes of this invention are new and they are useful for biomedical applications. The present invention is further detailed in the following Examples, which are offered by way of illustration and are not intended to limit the scope of the invention in any manner. Reliable computational methods for the prediction of the absorption maxima of some of the dyes were also established. Standard techniques well known in the art or the techniques specifically described below are utilized.

EXAMPLE 1

Figure 1:
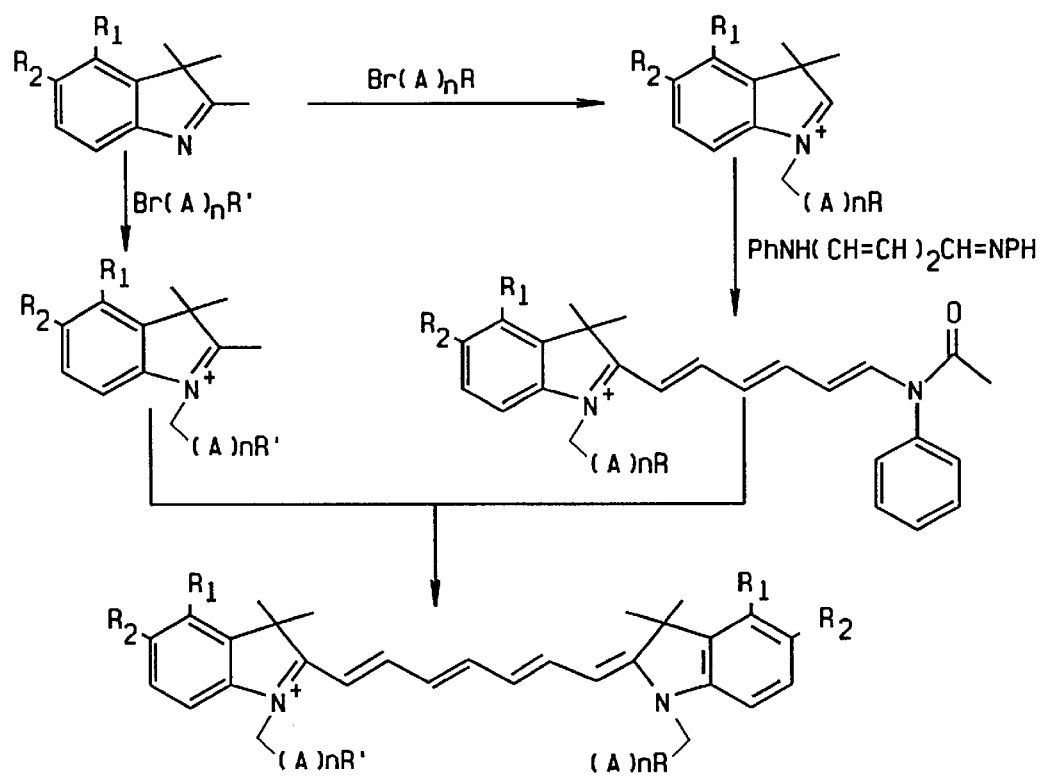
FIG. 1 shows the reactions in the synthesis of bis-carboxylates of this invention.

Synthesis of Bis(ethylcarboxymethyl)indocyanine Dye (FIG. 1, $R_1$, $R_2$=fused phenyl; A=$CH_2$, n=1 and R=R'=$CO_2H$)

A mixture of 1,1,2-trimethyl-[1H]-benz[e]indole (9.1 g, 43.58 mmoles) and 3-bromopropanoic acid (10.0 g, 65.37 mmoles) in 1,2-dichlorobenzene (40 mL) was heated at 110° C. for 12 hours. The solution was cooled to room temperature and the red residue obtained was filtered and washed with acetonitrile:diethyl ether (1:1) mixture. The solid obtained was dried under vacuum to give 10 g (64%) of light brown powder. A portion of this solid (6.0 g; 16.56 mmoles), glutaconaldehyde dianil monohydrochloride (2.36 g, 8.28 mmoles) and sodium acetate trihydrate (2.93 g, 21.53 mmoles) in ethanol (150 mL) were refluxed for 90 minutes. After evaporating the solvent, 40 mL of a 2 N aqueous HCl was added to the residue and the mixture was centrifuged and the supernatant was decanted. This procedure was repeated until the supernatant became nearly colorless. About 5 mL of water:acetonitrile (3:2) mixture was added to the solid residue and lyophilized to obtain 2 g of dark green flakes. The purity of the compound was established with $^1$H-NMR and LC-Mass spectrometry.

EXAMPLE 2

Synthesis of Bis(pentylcarboxymethyl)indocyanine Dye (FIG. 1, $R_1$, $R_2$=fused phenyl; A=$CH_2$, n=4 and R=R'=$CO_2H$)

A mixture of 1,1,2-trimethyl-[1H]-benz[e]indole (20 g, 95.6 mmoles) and 6-bromohexanoic acid (28.1 g, 144.1 mmoles) in 1,2-dichlorobenzene (250 mL) was heated at 110 C. for 12 hours. The green solution was cooled to room temperature and the brown solid precipitate formed was collected by filtration. After washing the solid with 1,2-dichlorobenzene and diethyl ether, the brown powder obtained (24 g, 64%) was dried under vacuum at room temperature. A portion of this solid (4.0 g; 9.8 mmoles), glutaconaldehyde dianil monohydrochloride (1.4 g, 5 mmoles) and sodium acetate trihydrate (1.8 g, 12.9 mmoles) in ethanol (80 mL) were refluxed for 1 hour. After evaporating the solvent, 20 mL of a 2 N aqueous HCl was added to the residue and the mixture was centrifuged and the supernatant was decanted. This procedure was repeated until the supernatant became nearly colorless. About 5 mL of water:acetonitrile (3:2) mixture was added to the solid residue and lyophilized to obtain about 2 g of dark green flakes. The purity of the compound was established with $^1$H-NMR and LC-Mass spectrometry.

EXAMPLE 3

Synthesis of Bisethylcarboxymethylindocyanine Dye (FIG. 1, $R_1=R_2=H$; $A=CH_2$, n=1 and $R=R'=CO_2H$)

This compound was prepared as described in Example 1 except that 1,1,2-trimethylindole was used as the starting material.

EXAMPLE 4

Synthesis of Bis(hexaethyleneglycolcarboxymethyl) indocyanine Dye (FIG. 1, $R_1=R_2=$fused phenyl: $A=CH_2OCH_2$, n=6 and $R=R'=CO_2H$)

This compound was prepared as described in Example 1 except that ω-bromohexaoxyethyleneglycolpropiolic acid was used in place of bromopropanoic acid and the reaction was carried out in 1,2-dimethoxypropane.

EXAMPLE 5

Figure 2:
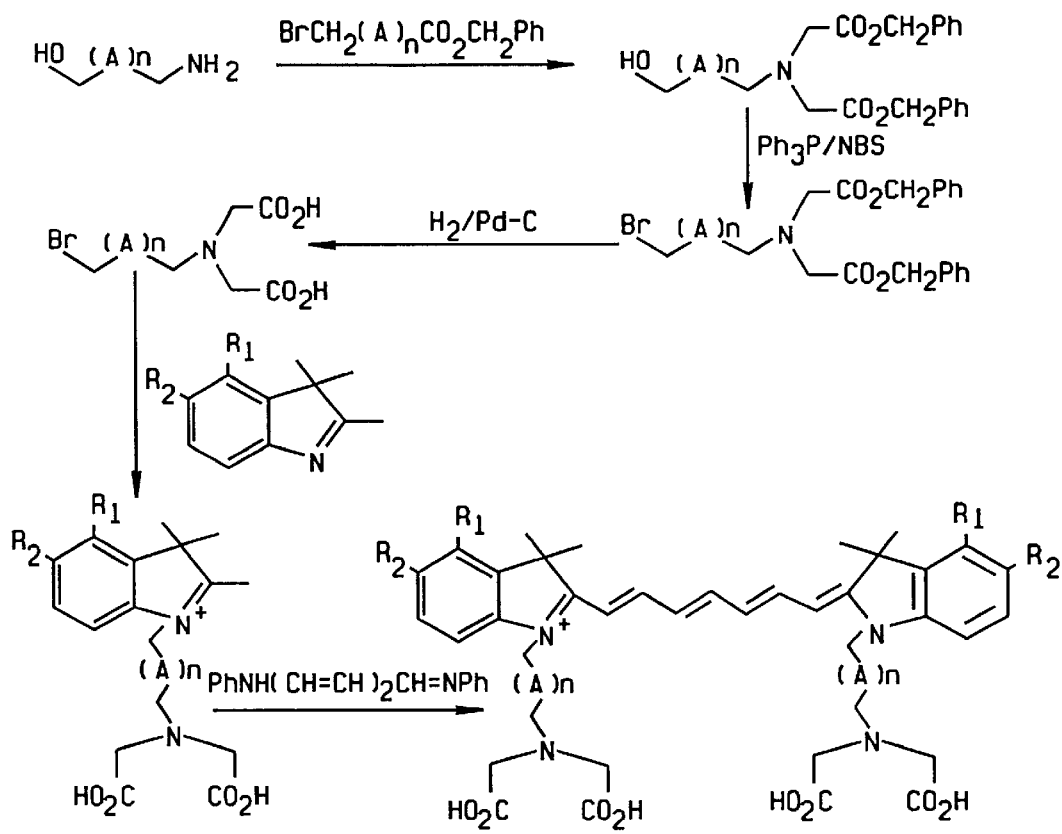
FIG. 2 shows the reactions in the synthesis of tetra-carboxylates of this invention.

Synthesis of Bisethylcarboxymethylindocyanine Dye (FIG. 2, $R_1=R_2=$fused phenyl; $A=CH_2$, and n=0)

A solution of 50 ml of dimethylformamide and benzyl bromoacetate (16.0 g, 70 mmol) was stirred in a 100 ml three-neck flask. Solid potassium bicarbonate (7.8 g, 78 mmol) was added. The flask was purged with argon and cooled to 0° C. with an ice bath. To the stirring mixture was added dropwise a solution of ethanolamine (1.9 g, 31 mmol) and 4 ml of dimethylformamide over 5 minutes. After the addition was complete the mixture was stirred for 1 hour at 0° C. The ice bath was removed and the mixture stirred at room temperature over night. The reaction mixture was partitioned between 100 ml of methylene chloride and 100 ml of saturated sodium bicarbonate solution. The layers were separated and the methylene chloride layer was again washed with 100 ml of saturated sodium bicarbonate solution. The combined aqueous layers were extracted twice with 25 ml of methylene chloride. The combined methylene chloride layers were washed with 100 ml of brine, and dried over magnesium sulfate. The methylene chloride was removed with aspirator vacuum at ca. 35° C., and the remaining dimethylformamide was removed with vacuum at about 45° C. The crude material was left on a vacuum line over night at room temperature.

The crude material from above was dissolved in 100 ml of methylene chloride at room temperature. Triphenylphosphine (8.91 g, 34 mmol) was added and dissolved with stirring. An argon purge was started and the mixture cooled to 0° C. with an ice bath. The N-bromosuccinimide (6.05 g, 34 mmol) was added portionwise over 2 minutes. The mixture was stirred for 1.5 hours at 0° C. The methylene chloride was removed with vacuum and gave a purple oil. This oil was triturated with 200 ml of ether with constant manual stirring. During this time the oil became very thick. The ether solution was decanted and the oil was triturated with 100 ml of ether. The ether solution was decanted and the oil was again triturated with a 100 ml portion of ether. The ether was decanted and the combined ether solutions allowed to stand for about 2 hours to allow the triphenylphosphine oxide to crystallize. The ether solution was decanted from the crystals and the solid washed with 100 ml of ether. The volume of the combined ether abstracts was reduced with vacuum until a volume of about 25 ml was obtained. This was allowed to stand over night at 0° C. Ether (10 ml) was added to the cold mixture which was mixed to suspend the solid. The mixture was percolated through a column of 45 g of silica gel and eluted with ether, 75 ml fractions were collected. The fractions that contained product by TLC were pooled and the ether removed with vacuum. This gave 10.1 g of crude product. The material was flash chromatographed on silica gel with hexane, changing to 9:1 hexane:ether. The product-containing fractions were pooled and the solvents removed with vacuum. This gave 7.4 g (57% yield) of pure product.

A mixture of 10% palladium on carbon (1 g) and a solution of the benzyl ester (10 g) in 150 ml of methanol was hydrogenolyzed at 25 psi for 2 hours. The mixture was filtered over celite and the residue was washed with methanol. The solvent was evaporated to give a viscous oil in quantitative yield.

Reaction of the bromide with 1,1,2-trimethyl-[1H]-benz[e]indole was carried out as described in Example 1.

EXAMPLE 6

Figure 3:
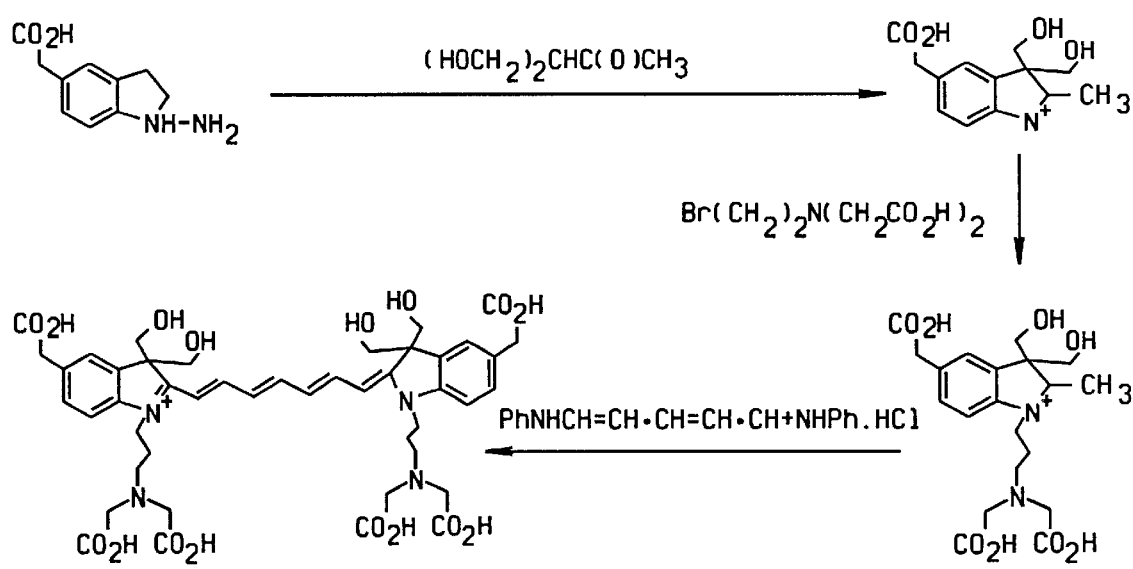
FIG. 3 shows the reactions in the synthesis of polyhydroxy-carboxylic acid cyanine dyes of this invention.

Bis(ethylcarboxymethyldihydroxyl)indocyanine Dye (FIG. 3)

The hydroxy-indole compound is readily prepared by literature method (P. L. Southwick, J. G. Cairns, L. A. Ernst, and A. S. Waggoner, One pot Fischer synthesis of (2,3,3-trimethyl-3-H-indol-5-yl)-acetic acid derivatives as intermediates for fluorescent biolabels. *Org. Prep. Proced. Int. Briefs*, 1988, 20(3), 279–284). Reaction of p-carboxymethylphenylhydrazine hydrochloride (30 mmol, 1 equiv.) and 1,1-bis(hydroxymethyl)propanone (45 mmole, 1.5 equiv.) in acetic acid (50 mL) at room temperature for 30 minutes and at reflux for 1 gives (3,3-dihydroxymethyl2-methyl-3-H-indol-5-yl)-acetic acid as a solid residue. The reaction of 3-bromopropyl-N,N-bis(carboxymethyl)amine, which was prepared as described in Example 5, with the intermediate indole and subsequent reaction of the indole intermediate with glutaconaldehyde dianil monohydrochloride (see Example 1) gives the desired product.

EXAMPLE 7

Synthesis of Bis(propylcarboxymethyl)indocyanine Dye (FIG. 4)

The intermediate 2-chloro-1-formyl-3-hydroxymethylenecyclohexane was prepared as described in the literature (G. A. Reynolds and K. H. Drexhage, Stable heptamethine pyrylium dyes that absorb in the infrared. *J. Org. Chem.*, 1977, 42(5), 885–888). Equal volumes (40 mL each) of dimethylformamide (DMF) and dichloromethane were mixed and the solution was cooled to −10° C. in acetone-dry ice bath. Under argon atmosphere, phosphorus oxychloride (40 mL) in dichloromethane was added dropwise to the cool DMF solution. The resulting solution was allowed to warm up to room temperature and refluxed for 6 hours. After cooling to room temperature, the mixture was poured into ice-cold water and stored at 4° C. for 12 hours.

About 8 g of yellow powder was obtained after filtration. Condensation of the cyclic dialdehyde with the indole intermediate is carried out as described in Example 1. Further the functionalization of the dye with bis (isopropylidene acetal protected monosaccharide by the method described in the literature (J. H. Flanagan, C. V. Owens, S. E. Romero, et al., Near infrared heavy-atom-modified fluorescent dyes for base-calling in DNA-sequencing application using temporal discrimination. *Anal. Chem.*, 1998, 70(13), 2676–2684).

EXAMPLE 8

Synthesis of Bis(ethylcarboxymethyl)indocyanine Dye (FIG. 5)

These dyes are prepared as described in Experiment 7. These dyes absorb in the infrared region. The typical example shown in FIG. 5 have estimated absorption maximum at 1036 nm.

EXAMPLE 9

Synthesis of Peptides

The procedure described below is for the synthesis of Octreotate. Other peptides were prepared by a similar procedure with minor modifications in some cases. These peptides were used to illustrate the ease of using dyes of this invention to prepare bioconjugates.

The octapeptide was prepared by an automated fluorenylmethoxycarbonyl (Fmoc) solid phase peptide synthesis using a commercial peptide synthesizer from Applied Biosystems (Model 432A SYNERGY Peptide Synthesizer). The first peptide cartridge contained Wang resin pre-loaded with Fmoc-Thr on a 25 μmole scale. Subsequent cartridges contained Fmoc-protected amino acids with side chain protecting groups for the following amino acids: Cys(Acm), Thr (t-Bu), Lys(Boc), Trp(Boc) and Tyr(t-Bu). The amino acid cartridges were placed on the peptide synthesizer and the product was synthesized from the C- to the N-terminal position. The coupling reaction was carried out with 75 μmoles of the protected amino acids in the presence of 2-(1H-benzotriazol-1-yl)-1,1,3,3-tetramethyluronium hexafluorophosphate (HBTU)/N-hydroxybenzotriazole (HOBt). The Fmoc protecting group was removed with 20% piperidine in dimethylformamide. After the synthesis was complete, the thiol group was cyclized with thallium trifluoroacetate and the product was cleaved from the solid support with a cleavage mixture containing trifluoroacetic acid (85%):water (5%):phenol (5%):thioanisole (5%) for 6 hours. The peptide was precipitated with t-butyl methyl ether and lyophilized with water:acetonitrile (2:3) mixture. The peptide was purified by HPLC and analyzed with LC/MS. The amino acid sequence of Octreotate is: D-Phe-Cys'-Tyr-D-Trp-Lys-Thr-Cys'-Thr, wherein Cys' indicates the presence of an intramolecular disulfide bond between two cysteine amino acids.

Octreotide was prepared by the same procedure: D-Phe-Cys'-Tyr-D-Trp-Lys-Thr-Cys'-Thr-OH, wherein Cys' indicates the presence of an intramolecular disulfide bond between two cysteine amino acids.

Bombesin analogs were prepared by the same procedure except that cyclization with thalium trifluoroacetate was not needed. Side-chain deprotection and cleavage from the resin was carried out with 50 μL each of ethanedithiol, thioanisole and water, and 850 μL of trifluoroacetic acid. Two analogues were prepared: Gly-Ser-Gly-Gln-Trp-Ala-Val-Gly-His-Leu-Met-NH$_2$ and Gly-Asp-Gly-Gln-Trp-Ala-Val-Gly-His-Leu-Met-NH$_2$.

Cholecystokinin octapeptide analogs were prepared as described for Octreotate without the cyclization step. Three analogs were prepared: Asp-Tyr-Met-Gly-Trp-Met-Asp-Phe-NH$_2$; Asp-Tyr-Nle-Gly-Trp-Nle-Asp-Phe-NH$_2$; D-Asp-Tyr-Nle-Gly-Trp-Nle-Asp-Phe-NH$_2$;

Neurotensin analog was prepared as described for Octreotate without the cyclization step: D-Lys-Pro-Arg-Arg-Pro-Tyr-Ile-Leu.

EXAMPLE 10

Synthesis of Peptide-Dye Conjugates

The method described below is for the synthesis of Octreotate conjugates but a similar procedure is used for the synthesis of other peptide-dye conjugates.

The Octreotate was prepared as described in Example 6 but the peptide was not cleaved from the solid support and the N-terminal Fmoc group of Phe was retained. The thiol group was cyclized with thallium trifluoroacetate and the Phe was deprotected to liberate the free amine. Bisethylcarboxymethylindocyanine dye (53 mg, 75 μmoles) was added to an activation reagent consisting of a 0.2 M solution of HBTU/HOBt in DMSO (375 μL), and 0.2 M solution of diisopropylethylamine in DMSO (375 μL). The activation was complete in about 30 minutes and the resin-bound peptide (25 μmoles) was added to the dye. The coupling reaction was carried out at room temperature for 3 hours. The mixture was filtered and the solid residue was washed with DMF, acetonitrile and THF. After drying the green residue, the peptide was cleaved from the resin and the side chain protecting groups were removed with a mixture of 85% trifluoroacetic acid, 2.5% water, 2.5% thioanisole and 2.5% phenol. The resin was filtered and cold t-butyl methyl ether (MTBE) was used to precipitate the dye-peptide conjugate which was dissolved in acetonitrile:water (2:3) mixture and lyophilized. The product was purified by HPLC to give the monoOctreotate-Bisethylcarboxymethylindocyanine dye (Cytate 1, 80%) and the bisOctreotate-Bisethylcarboxymethylindocyanine dye (Cytate 2, 20%). The monoOctreotate conjugate can be obtained almost exclusively (>95%) over the bis conjugate by reducing the reaction time to 2 hours. However, this also leads to incomplete reaction and the free Octreotate must be carefully separated from the dye conjugate in order to avoid saturation of the receptors by the non-dye conjugated peptide.

Octreotate-bispentylcarboxymethylindocyanine dye was prepared as described above with some modifications. Bispentylcarboxymethylindocyanine dye (60 mg, 75 μmoles) was added to an activation reagent consisting of a 0.2 M solution of HBTU/HOBt in DMSO (400 μL), and 0.2 M solution of diisopropylethylamine in DMSO (400 μL). The activation was complete in about 30 minutes and the resin-bound peptide (25 μmoles) was added to the dye. The reaction was carried out at room temperature for 3 hours. The mixture was filtered and the solid residue was washed with DMF, acetonitrile and THF. After drying the green residue, the peptide was cleaved from the resin and the side chain protecting groups were removed with a mixture of 85% trifluoroacetic acid, 2.5% water, 2.5% thioanisole and 2.5% phenol. The resin was filtered and cold t-butyl methyl ether (MTBE) was used to precipitate the dye-peptide conjugate which was dissolved in acetonitrile:water (2:3) mixture and lyophilized. The product was purified by HPLC to give Octreotate-1,1,2-trimethyl-[1H]-benz[e]indole propanoic acid conjugate (10%), monoOctreotate-bispentylcarboxymethylindocyanine dye (Cytate 3, 60%) and bisOctreotate-bispentylcarboxymethylindocyanine dye (Cytate 4, 30%).

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A method for restoring in vivo or in vitro fluorescence by adding one to fifty percent biocompatible organic solvents to the diagnostic or therapeutic compositions of dye molecules wherein said dye molecules are represented by the formula:

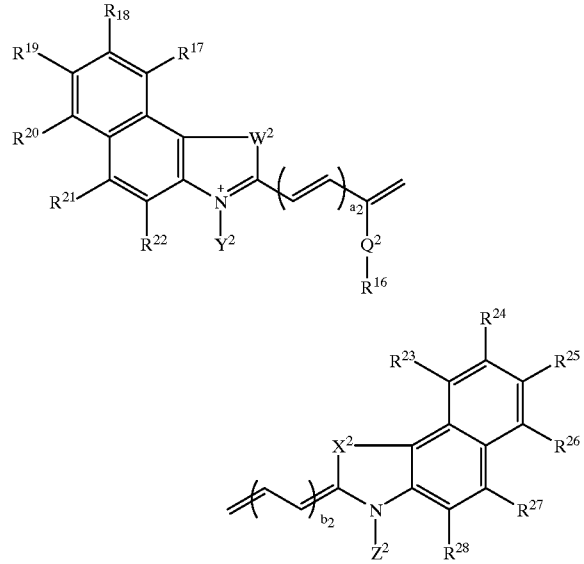

wherein $a_2$ and $b_2$ are independently 0 to 5; $W^2$ and $X^2$ are independently selected from the group consisting of $C((CH_2)_{zz}OH2$, $C((CH_2)_{zz}CO_2H)_2$, $C((CH_2)_{zz}NR_{pp}R_{pz})_2$; and zz is from 1 to 5; $R_{pp}$ and $R_{pz}$ are independently selected from the group consisting of $-(CH_2)_c-CO_2H$, $-CH_2-(CH_2-O-CH_2)_d-CH_2-CO_2H$, $-(CH_2)_g-N(R^{14})-(CH_2)_h-CO_2H$, and $-(CH_2)_i-N(R^{15})-CH_2-(CH_2-O-CH_2)_j-CH_2-CO_2H$; $Q^2$ is a single bond or is selected from the group consisting of $-O-$, $-S-$, $-Se-$, and $NR^{13}$; $Y^2$ and $Z^2$ are independently selected from the group consisting of $-(CH_2)_c-CO_2H$, $-CH_2-(CH_2-O-CH_2)_c-CH_2-CO_2H$, $-(CH_2)_e-NH_2$, $-CH_2-(CH_2-O-CH_2)_f-CH_2-NH_2$, $-(CH_2)_g-N(R^{14})-(CH_2)_h-CO_2H$, and $-(CH_2)_i-N(R^{15})-CH_2-(CH_2-O-CH_2)_j-CH_2-CO_2H$; $R^{13}-R^{16}$ are independently selected from the group consisting of -hydrogen, C1–C10 alkyl, C1–C10 alkoxyl, $-(CH_2)_d-CO_2H$, $-CH_2(CH_2-O-CH_2)_e-CH_2CO_2H$, $-(CH_2)_f-NH_2$, and $-CH_2-(CH_2-O-CH_2)_g-CH_2NH_2$; c, e, g, h, and i are independently 1 to 10; d, f and j are independently 1 to 100; and $R^{17}$ to $R^{28}$ are selected from the group consisting of hydrogen, C1–C10 alky, hydroxyl, C1–C10 alkoxyl, amino, C1–C10 aminoalkyl, cyano, nitro, and halogen.

2. The method of claim 1 wherein said dye molecule is dissolved in a medium comprising one to 50 percent dimethyl sulfoxide (DMSO).

3. The composition of claim 1 wherein $a_2$ and $b_2$ are independently 0 to 3; $Q^2$ is a single bond; $R^{16}$ to $R^{28}$ are hydrogens; $W^2$ and $X^2$ are independently selected from the group consisting of $C((CH_2)_{zz}OH)_2$, $C((CH_2)_{zz}CO_2H)_2$, and $C((CH_2)_{zz}NR_{pp}R_{pz})_2$; $Y^2$ and $Z^2$ are independently selected from the group consisting of $-(CH_2)_c-CO_2H$, $-CH_2-(CH_2-O-CH_2)_d-CH_2-CO_2H$, $-(CH_2)_g-N(R^{14})-(CH_2)_h-CO_2H$ and $-(CH_2)_i-N(R^{15})-CH_2-(CH_2-O-CH_2)_j-CH_2-CO_2H$; $R_{pp}$ and $R_{pz}$ are independently selected from the group consisting of $-(CH_2)_c-CO_2H$, $-CH_2-(CH_2-O-CH_2)_d-CH_2-CO_2H$, $-(CH_2)_g-N(R^{14})-(CH_2)_h-CO_2H$, and $-(CH_2)_i-N(R^{15})-CH_2-(CH_2-O-CH_2)_j-CH_2-CO_2H$; c, e, g, h, i, and zz are independently 1 to 5; d, f and j are independently 1 to 100; and $R^{14}$ and $R^{15}$ are independently selected from the group consisting of -hydrogen, C1–C10 alkyl, C1–C10 alkoxyl $-(CH_2)_d-CO_2H$, $-CH_2-(CH_2-O-CH_2)_e-CH_2CO_2H$, $-(CH_2)_f-NH_2$, and $-CH_2-(CH_2-O-CH_2)_g-CH_2-NH_2$.

4. The composition of claim 3 wherein $a_2$ and $b_2$ are 3; $Q^2$ is a single bond; $R^{18}$ to $R^{28}$ are hydrogens; $W^2$ and $X^2$ are independently selected from the group consisting of $-C((CH_2)_{zz}OH)_2$, $C((CH_2)_{zz}CO_2H)_2$ and $C((CH_2)_{zz}NR_{pp}R_{pz})_2$; and $Y^2$ and $Z^2$ are the same and are selected from the group consisting of $-(CH_2)_c-CO_2H$, $-CH_2(CH_2-O-CH_2)_d-CH_2CO_2H$ and $-(CH_2)_g-N(R^{14})-(CH_2)_h-CO_2H$.

* * * * *